United States Patent [19]
Popescu et al.

[11] Patent Number: 5,464,580
[45] Date of Patent: Nov. 7, 1995

[54] PROCESS OF STERILIZATION

[75] Inventors: Miron G. Popescu, Trevose, Pa.; David F. Bekus, Pittstown, N.J.; Shakti Routh, Ringoes, N.J.; Luis E. Vera, Bergenfield, N.J.; Thomas A. Clark, Cranford, N.J.

[73] Assignee: Ethicon, Inc., Somerville, N.J.

[21] Appl. No.: 251,874

[22] Filed: Jun. 1, 1994

[51] Int. Cl.⁶ ........................... B65B 55/02
[52] U.S. Cl. .................. 422/34; 422/1; 422/40; 422/297; 422/300
[58] Field of Search ................ 422/34, 40, 25, 422/297, 300, 1; 454/187, 195, 193

[56] References Cited

U.S. PATENT DOCUMENTS

| | | | |
|---|---|---|---|
| 3,767,362 | 10/1973 | Griffin | 21/58 |
| 3,815,315 | 6/1974 | Glick | 422/34 |
| 4,517,167 | 5/1985 | Popescu et al. | 423/245 |
| 5,101,813 | 4/1992 | Trick | 600/40 |
| 5,128,101 | 7/1992 | Boynton | 422/31 |
| 5,222,978 | 6/1993 | Kaplan et al. | 606/228 |
| 5,341,922 | 8/1994 | Cerwin et al. | 206/63.3 |

Primary Examiner—Timothy M. McMahon
Assistant Examiner—N. Bhat
Attorney, Agent, or Firm—Michael Q. Tatlow

[57] ABSTRACT

A sterilization process for moisture sensitive products employing a closed system and moving unsealed products to be sterilized through a sterilizer, degassing chamber and a storage and package sealing chamber while maintaining the products in a dry pathogen free atmosphere.

7 Claims, 3 Drawing Sheets

5,464,580

PROCESS OF STERILIZATION

BACKGROUND OF THE INVENTION

The present invention relates to the treatment of articles, particularly medical articles such as absorbable sutures, clips and staples, by subjecting them to a gaseous sterilizing agent to sterilize the products. The particular gaseous sterilizing agent employed is ethylene oxide which is a well known gas used as a sterilizing agent.

The present process is particularly useful in the sterilization of moisture sensitive medical products, that is, products that will degrade if exposed to atmospheric moisture. This type of product includes sutures, ligating clips and staples made from polymeric materials which will absorb over time in an animal or human body. These polymeric materials include homopolymer and copolymers of glycolide and lactide; polymers have dioxanone linkages, and copolymers of a dioxanone with other monomers such as caprolactone; and mixtures of such polymers and copolymers.

Generally, these polymers are very sensitive to moisture and are broken down in the body by a hydrolytic degradation or a combination of hydrolytic degradation and other activity. It is therefore necessary that products made from such polymers be packaged in air tight containers which are substantially impervious to water vapor including atmospheric moisture, to prevent the degradation of the product during storage. Generally, these packages are laminates which include one or more metallic foil layers. The atmospheric moisture cannot penetrate the metallic foil layer of the package and therefore these products have long term storage stability. Some of these absorbable polymers are also degraded by oxygen. The metal foil packaging materials also prevent oxygen from penetrating the package and contacting the product during storage. Medical products made from oxygen degradable polymers are usually packaged in a nitrogen or other inert gas atmosphere to limit degradation during storage.

An example of this type of a package that is commonly used such products is shown in U.S. Pat. No. 3,815,315 which discloses an absorbable suture material sterilized with an ethylene oxide containing gas and packaged in a package with a metallic foil layer.

The prior art sterilization process which is disclosed in U.S. Pat. No. 3,815,315 comprises placing the surgical product in a packaging material which is substantially impervious to moisture vapor. The package is sealed on three sides with the fourth side open to the atmosphere. This package is then placed in a bacteria proof transfer container which is permeable to the sterilizing gas but not permeable to bacteria. The transfer container holding the open suture package is then placed in a ethylene oxide sterilizing chamber. Ethylene oxide in combination with a fluorocarbon gas diluent or other diluent is added to the sterilizer. After sterilization is effected, the transfer container containing the open package is placed in a dryer and the product is dried under heat and vacuum, to remove any water from the suture. The transfer container is removed to a dry room where it is stored in a substantially moisture free atmosphere until the final sealing of the package. At that time, the transfer container is transferred to a sterile area the foil package containing the suture is removed from the transfer container and the gas is removed from the package and replaced with an anhydrous gas and the foil laminate is sealed. The foil package is then placed in an outer envelope which may be moisture previous and the space between the two envelopes is then sterilized to sterilize the outer surface of the inner metal foil package.

The above mentioned prior art process of sterilization employs an intermediate packaging step, the bacteria proof transfer container, to protect the sterility of the product from the point of sterilization to the point where the package is finally sealed. The foil package must be removed from the transfer container before it can be sealed. This step may introduce some contamination of the package or may introduce moisture into the package after the product has been dried.

Prior art sterilization techniques employing ethylene oxide generally use a single vessel or chamber which is put through successive steps of loading of the item to be sterilized, evacuation of the vessel, subjecting the item to be sterilized to a sterilizing gas for the required time period to effect the sterilization and the subsequent removal of the sterilizing gas from the vessel and subjecting the packaged product to out-gassing or a vacuum removal of the ethylene oxide from the package. Since ethylene oxide is a toxic material it is not desired in the finished product or package. Generally, packaged products are subjected to out gassing or aeration to remove the ethylene oxide from the package. Examples of ethylene oxide sterilization include the process as described in the above mentioned U.S. Pat. No. 3,815,315 as well as the process described in U.S. Pat. Nos. 3,068,864; 3,767,362 and 5,128,101. In addition to the steps mentioned above, there is also a step of humidifying the product to be sterilized prior to the contacting of the product with the sterilizing gas. In the situations where the product to be sterilized is not subject to degradation by water or oxygen, the package can be made from a material that allows passage of the sterilizing gas and air but prevents the passage of bacteria. Therefore, the package may be completely sealed and sterilized and then aerated without danger of the product being contaminated during processing.

Sterilization with ethylene oxide has also been carried out in separate unconnected vessels or chambers, for example; a preconditioning vessel, a sterilization vessel and an out gassing vessel. The product to be sterilized is physically moved through the ambient atmosphere from one vessel to the next vessel in the sterilization process. This type of sterilization has been employed for packages which are completely sealed prior to sterilization.

One of the problems with the use of ethylene oxide gas as a sterilizing agent is that mixtures of ethylene oxide and oxygen or air are explosive. Care must be exercised with ethylene oxide to avoid the possibility of inadvertently forming an explosive concentration of ethylene oxide in air. To reduce this possibility, ethylene oxide is usually employed as a sterilizing gas in a mixture with an inert gas such as a fluorocarbon, carbon dioxide and in some instances, nitrogen. A negative aspect of such lower concentration of ethylene oxide in sterilizing gas mixtures is that the sterilization time is generally extended as the concentration of the ethylene oxide is reduced.

SUMMARY OF THE PRESENT INVENTION

The present invention is directed to a process of sterilizing a moisture sensitive product, in which the product to be sterilized is placed in an open package made from a moisture impervious material, is sterilized and dried and is maintained in a low humidity atmosphere and in a sterile state until the package containing the moisture sensitive product is sealed. The sterilization process includes multiple containment vessels or chambers and transfer bays between the chambers to allow the products which are to be sterilized to be transferred from one chamber to another without passing through the ambient atmosphere outside of the sterilization apparatus. As the system is a closed system, it is readily maintained in an aseptic condition by periodic decontamination with hydrogen peroxide, formaldehyde, glutaraldehyde or other liquid or gaseous disinfecting agent. The preferred decontamination agent is hydrogen peroxide.

The medical products of the type to which the present invention are directed are products that are absorbed in a human or animal body. These products include wound closure products such as sutures, clips or staples, and absorbable orthopedic products such as absorbable nails, pins, screws and bone plates. As mentioned above, these products are generally made from polymers of glycolide or lactide or copolymers of glycolide or mixtures of such polymers and lactide or polydioxone polymers or copolymers or physical mixtures of polymers of polydioxone with polymers or copolymers of glycolide and/or lactide or with other polymers. Products made from such polymers are similar in that they begin to deteriorate when they are exposed to moisture. If these products come in contact with moisture prior to the time they are to be used, the products will rapidly deteriorate and loose their strength. Particularly, the desirable property of in-vivo tensile strength retention for sutures will be rapidly lost if the products are exposed to moisture for any significant time period prior to use. Since products of this type are sensitive to both moisture and heat, they cannot be sterilized with steam. In addition, cobalt radiation sterilization has a tendency to degrade these materials and for that reason cobalt radiation is not used to sterilize products of this type. These products are generally sterilized with ethylene oxide gas. The sterilizing gas is usually in the form of a mixture of ethylene oxide and an inert gas. Common inert gases are fluorocarbons such as 1,2,2,2-pentafluoroethane or 1,2,2,2-tetrafluoroethane or 1-chloro-1,2,2,2-tetrafluoroethane or carbon dioxide or nitrogen.

The packaging material most commonly used for moisture sensitive medical products includes a heat sealable metal foil. The heat sealable foil is usually a laminate of polyethylene, or other polyolefin, coated on a metal foil, such as aluminum in such a manner that the application of heat to the foil will cause a melting of the coating and will cause the portions of the foil to which heat is applied to adhere together. Packages of the type are disclosed in the previously mentioned U.S. Pat. No. 3,815,315.

As previously indicated, the sterilization technique disclosed in U.S. Pat. No. 3,815,315 includes the step of removing open packages from a sterilizer and physically moving them through the ambient atmosphere to a subsequent processing step. This movement of the product could lead to contamination of the product by pathogens contained in the atmosphere or the product could absorb moisture vapor and begin to degrade. The present process uses at least three chambers with transfer bays between the chambers so that product to be sterilized can move from one chamber to another through the transfer bays without coming into contact with the ambient atmosphere. In addition, the products may be sealed automatically in an extremely low humidity chamber without the product being exposed to moisture in the ambient atmosphere.

Another advantage of the present process is the capability of using high concentrations of ethylene oxide, up to 100% ethylene oxide, with a minimal risk of forming an explosive mixture of ethylene oxide and air.

DETAIL DESCRIPTION OF THE INVENTION

Figure 1:
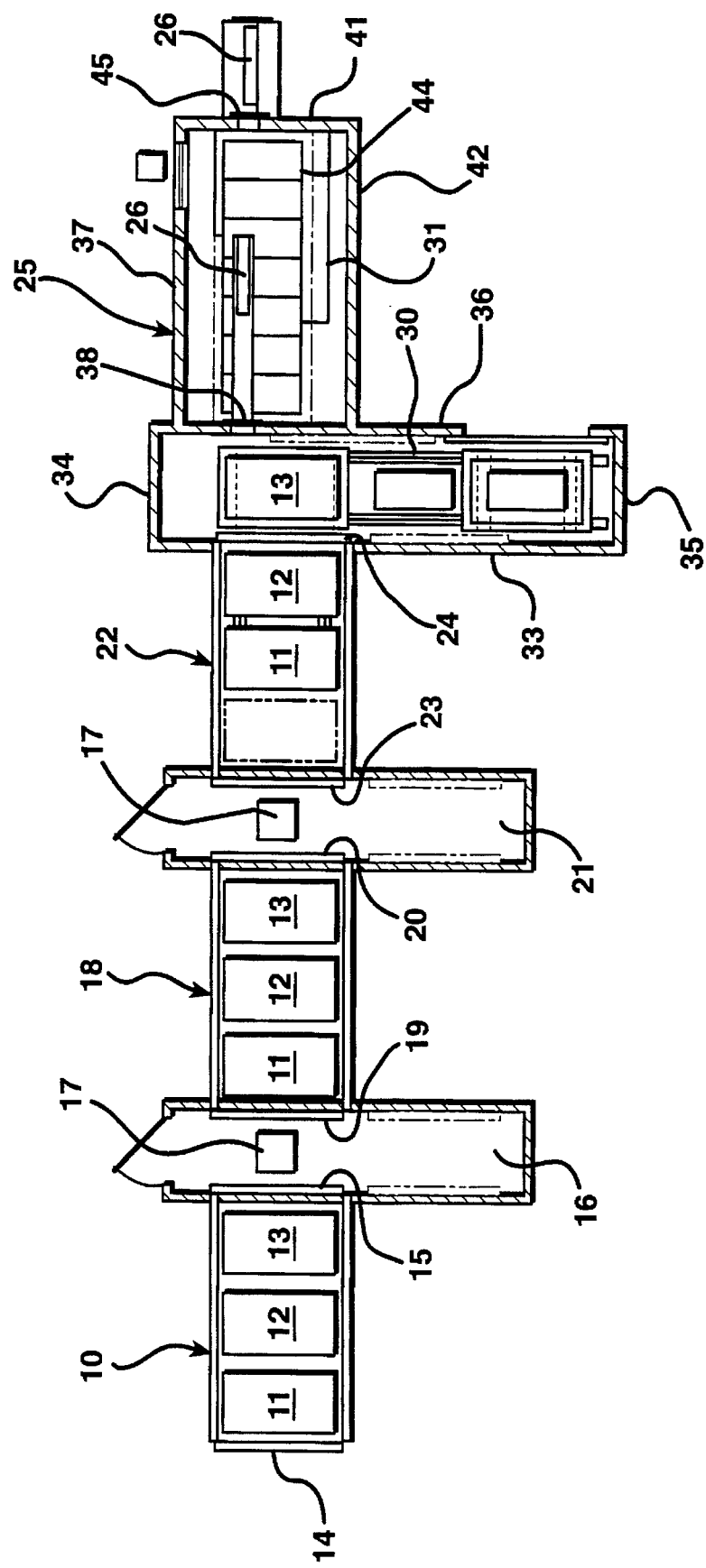
FIG. 1 is schematic representation of a top plan view of the apparatus that could be employed to carry out the process of the present invention.

The type of process equipment that could be used to carry out the process of the present invention is illustrated in the schematic illustration of FIG. 1. In FIG. 1, 10 is a sterilization chamber. The rectangular boxes 11, 12 and 13 within the chamber 10 represent moveable pallets on which the product to be sterilized is carried through the process. The sterilizer chamber 10 has sliding doors 14 and 15, one at each end of the chamber for loading and unloading of the pallets containing the product to be sterilized. The door 15 opens into a transfer bay 16 which may contain therein a automatic device 17 capable of moving the pallets from the sterilizer chamber into a vacuum dryer chamber 18. The automatic device could be a robot device or the pallets could be mounted on wheels and guided by rails when moved between chambers. The vacuum drying chamber is also capable of holding three pallets, 11, 12 and 13 containing a product which has been sterilized and which is be dried in the vacuum drying chamber. The vacuum drying chamber also has two sliding doors, 19 and 20, one at each end of the chamber. The door 19 is opened to receive pallets from the sterilizer and the door 20 is opened to move products from the vacuum drying chamber through the transfer bay 21 after drying. Transfer bay 21 is substantially identical to the transfer bay 16, and includes a similar automatic device 17 to move the pallets from the vacuum drying chamber 18 to the dry hold chamber 22. There is also a dry hold chamber 22 which receives the vacuum dried product from the transfer bay 21 to hold until the package containing the medical products can be sealed, or until the product is transferred to a forth chamber where the package will be sealed. There are sliding doors 23 and 24 in the dry hold chamber 22 to allow passage of the pallets into and out of the chamber.

The pallets 11, 12 and 13 contain trays 26 (shown in FIG. 2) in which the product to be sterilized is stored. The function of the trays is to hold the product packages in a position with the open end of the package unobstructed to allow the sterilizing gas to flow into the package and to have the package positioned for ease in subsequent sealing. The pallet containing the product is moved from the dry hold chamber 22 into a sealing room 25 which contains automatic equipment to seal the suture packages. The procedure to seal the packages is to take a tray 26 from the pallet and move the tray through a package sealing machine to seal the open edge or edges of the foil package before the packages are transferred out of the sealing room.

The dry hold chamber can be a single large chamber or multiple chambers with transfer mechanisms to automatically transfer product between the separate chambers. The dry hold chamber or space 30 (see FIGS. 1 and 2) can be considered to include chamber 22; the elevator chamber or space defined by walls 33, 34, 35 and 36 and the sealing chamber 31 defined by walls 36, 37, 41 and 42. The space 30 includes an elevator 32 which can lift a pallet 11, 12 or 13 to align the product containing trays 26 on the pallet with an air lock door 38 in the wall 36. The tray 26 can be moved through a sliding door 38 into the sealing space 31 where packages contained on the trays may be automatically sealed. An automatic sealing machine 44 receives the trays and heat seals the edge or edges of the foil laminate package containing the sterilized product. The tray 26 can then be removed from the space 31 through a small sliding door 45 into the ambient atmosphere or into an air lock (not shown) and then into the ambient atmosphere. The empty pallets may be removed from the chamber 30 through a door (not shown) into an antechamber or air lock and then out the system. The purpose of the antechamber or air lock is to prevent ambient air from entering the system.

Figure 2:
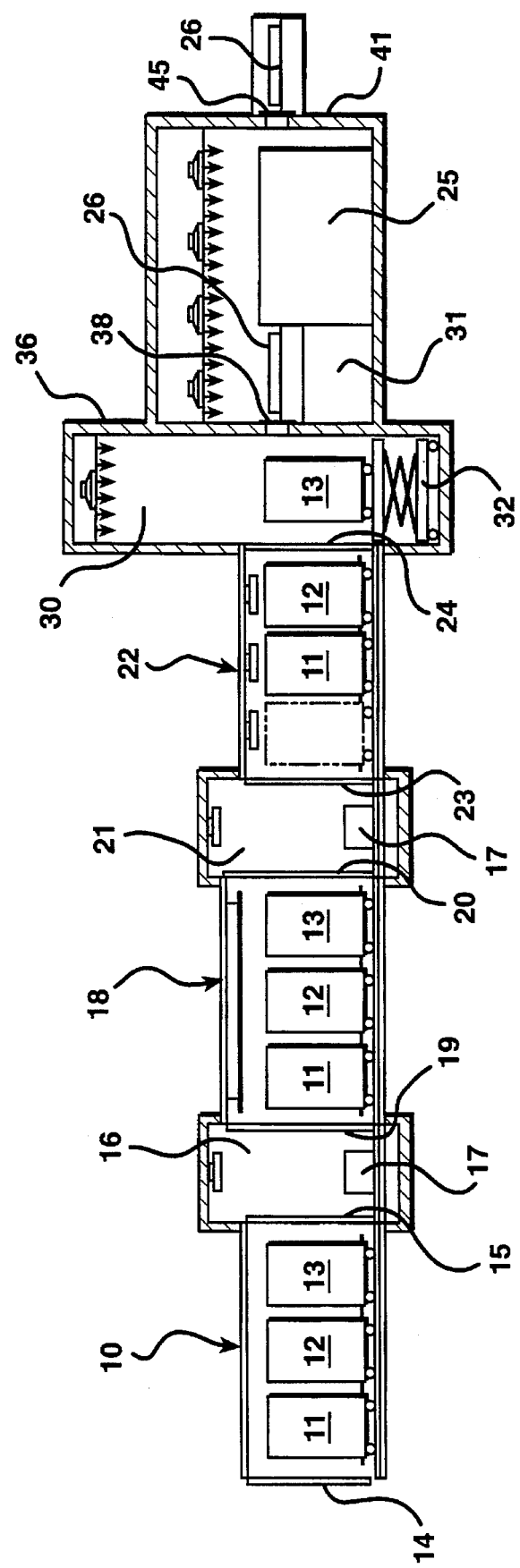
FIG. 2 is a schematic representation of a side view of the apparatus shown in FIG. 1.

The process steps of the present invention can be understood with reference to FIGS. 1 and 2. In the present process, the sterilization cycle begins by opening the doors to the sterilization vessel and the product to be sterilized, on the pallets, is introduced into the sterilizing vessel through door 14 at one end of the vessel. Prior to the start of the cycle, the atmosphere in the vessel will be nitrogen remaining from the end of the previous sterilization cycle. The door 14 is then closed and an external jacket on the sterilizer is heated to a temperature of about 25° C. A vacuum is then drawn on the vessel to approximately 1.8 to 6 KPa. Pressure in the vessel is then reduced to 1.8 KPa and steam is added to humidify the product to be sterilized. The steam is added by introducing steam until the pressure in the vessel is approximately 2.1 KPa. When the pressure in the vessel reaches 2.1 KPa, the steam control valve closes. The absorption of steam by the product reduces the pressure. When the pressure in the vessel is reduced to 2.0 KPa, the valve again opens. These cycles are repeated a number of times, generally not less than 5 or more than 45, so that the total time that the steam valve is in an open position is generally not less then 60 minutes or more than 90 minutes.

Following the preconditioning or humidification cycle set forth above, the chamber is then pressurized by the introduction of dry nitrogen gas to a pressure of between 46 and 48 KPa. When the desired pressure is reached, pure ethylene oxide is introduced into the chamber until the pressure in the chamber reaches about 95 KPa plus or minus approximately 1.0 KPa. The ethylene oxide is held in the chamber until the sterilization is completed. Generally, this is between approximately 360 and 600 minutes for sutures. The time required to sterilize other medical products in the chamber will vary somewhat depending on the type of product and the packaging, but is usually not more than 720 minutes. After the desired contact with the ethylene oxide is completed, the vessel is evacuated to a pressure of approximately 0.07 KPa and the pressure is maintained for approximately two hours to remove residual moisture and ethylene oxide from the sterilized product. The pressure is returned to atmospheric pressure by the admission of nitrogen gas at a temperature of approximately 21° to 32° C. The use of pure nitrogen or other inert gas rather than air to repressurize the vessel significantly reduces the possibility of inadvertently forming an explosive mixture of ethylene oxide and oxygen.

The pallets containing the product which is now sterilized and are to be dried are then transferred from sterilizer chamber 10 through a transfer bay to the dryer chamber 18. The transfer bay is charged with nitrogen gas having a dew point of approximately −30° C. before the sterilizer chamber doors are opened. The transfer is accomplished by opening the exit door 15 in the sterilizer chamber 10 and transferring the pallets with a robot 17 from the sterilizer through the transfer bay 16 and into the drying chamber 18. Any gas in the sterilizer chamber 10 will be at a pressure higher than the pressure of the transfer bay and will move from the sterilizer to the transfer bay when the exit door of the sterilizer is open. Since the transfer bay contains only dry nitrogen gas, the danger of any ethylene oxide being mixed with oxygen in explosive proportions is eliminated.

After the pallets are transferred into the drying chamber 18, the exit door 15 of the sterilizer can be closed and new pallets containing a product to be sterilized can be loaded into the sterilizer 10 and a new sterilization cycle started.

The drying chamber 18 is a vacuum dryer which is used to eliminate residual ethylene oxide and moisture from the sterilized product after the sterilization has been completed. Since ethylene oxide is toxic, it is substantially removed from the sterilized product after the sterilization is completed. The jacket temperature of the dying chamber is maintained at a temperature of 48° to 52° C. throughout the drying cycle. The drying cycle itself includes reducing the pressure in the drying vessel to approximately 0.01 KPa or less. Dry nitrogen is then added to the vessel to a pressure of approximately 100 KPa. The pressure is then reduced in the drying chamber to a pressure of less than 0.01 KPa and the cycle of adding dry nitrogen and reducing the pressure is repeated for a number of cycles. A typical cycle includes the steps of increasing the pressure with nitrogen to approximately 100 KPa, evacuating the chamber to a pressure of approximately 0.03 KPa over a period of 120 minutes, reintroducing nitrogen to a pressure of 100 KPa and circulating the nitrogen for approximately 90 minutes, evacuating the chamber to a pressure of approximately 0.01 KPa over a period of approximately 100 minutes and maintaining that pressure for an additional 240 minutes. At the end of the total cycle, which takes approximately 12 hours, the vessel is pressurized with dry nitrogen gas.

When the drying cycle has been completed, the pallets are removed from the drying chamber 18 through a transfer bay 21 using a robot 17 into a third chamber which is a dry hold chamber 22. The transfer bay 21 contains dry nitrogen having a dew point of not more than minus 52° C. before the drying chamber door 20 is opened. This is to prevent moisture from being added to the product after it has been dried. The pallets containing the product are removed from the drying chamber 18 through the exit door 20 and the exit door is then closed. The pallets containing the product are moved through the transfer bay 21 into the dry hold chamber 22 which also contains a nitrogen atmosphere with dry nitrogen having a dew point of not more than minus 52° C. The dry hold chamber has a controlled atmosphere which is maintained at a selected temperature and humidity and gas content depending upon the product undergoing sterilization. If the product to be sterilized is made from a polydioxonone polymer, the chamber will be maintained at all times at an atmosphere of dry nitrogen as an oxygen atmosphere is detrimental to the stability of the polydioxonone polymers. If the product to be sterilized is made from polymers or copolymers of glycolide or lactide, a atmosphere containing oxygen is permissible. In any event, the product to be sterilized is now put through a sealing device to automatically seal the packages containing the product. The packages are then removed from the sterilizer through an air chamber or through an exit door in the wall of the dry hold chamber which prevents the entry of atmospheric air.

Figure 3:
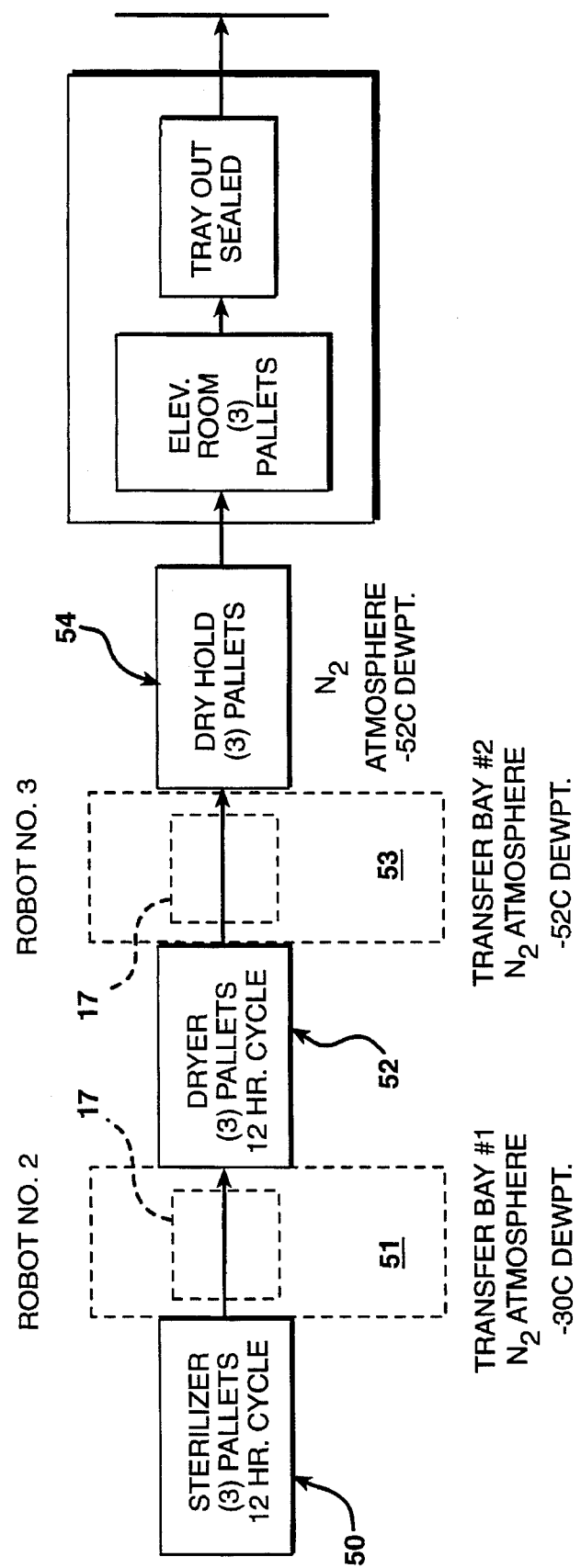
FIG. 3 is a block diagram showing the process of the present invention.

The blocked diagram of FIG. 3 is another illustration of the process of the present invention. The block 50 indicates a sterilization step or cycle of the process. The sterilizing cycle, including the loading and unloading takes approximately 12 hours. After the sterilization is completed, pallets holding the product to be dried are moved through the transfer bay, block 51. The transfer chamber initially has a nitrogen atmosphere having a dew point of at least minus 30° C. to provide a dry oxygen free atmosphere. The pallets are move through the transfer chamber into a drying chamber where the vacuum drying step or cycle of the process, indicated as block 52, is performed. The drying cycle dries the product as previously indicated and after completion of the cycle, which also takes 12 hours, the product is passed through a second transfer bay, block 53. The second transfer bay has a nitrogen atmosphere at a dew point of minus 52 degrees C. The reason for the lower dew point in the second transfer bay is because the product has been dried after leaving the drying chamber and in order to maintain the product in a dry condition, the moisture content of the atmosphere of the second transfer bay should be as low as possible. A dew point of minus 30 degrees C represents a moisture level equivalent to approximately 1.641 grains of water per pound of gas and a relative humidity of 1.52% at 70° F. A dew point of minus 52 degrees C is preferred and is equivalent to a moisture level of approximately 0.1342 grains per pound of gas or a relative humidity of about 0.123% at 70° F.

The pallets are transferred through the second transfer bay into a dry hold chamber, indicated as block 54. It is in the dry hold chamber that the packages contained in the pallets are held until the packages are finally sealed. As previously indicated, the dry hold chamber may be a single chamber or preferably multiple chambers, containing equipment to move the unsealed product containing packages from the pallets to an automatic sealing machine and subsequently out of the dry hold chamber into the ambient atmosphere for subsequent processing. The dry hold chamber can be maintained in a nitrogen atmosphere having a dew point of minus 52° C. If the product to be sterilized does not require such stringent conditions, the atmosphere can be suitably adjusted to a level which is adequate to maintain the stability of the product after packaging. As indicated in the block diagram and as previously described, there is an auto sealing device in the extended dry hold chamber that will automatically seal the open end of the metal foil packages. The metal foil packages are generally maintained in a tray on the pallet. After the package is sealed, the trays can be passed through the walls of the sealing chamber to the atmosphere. The passage through the wall is such that the atmosphere can be maintained in the dry hold chamber as the pressure in the sealing chamber is greater than the ambient pressure. The pallets on which the trays are contained can also be removed from the auto sealing chamber without compromising the atmosphere in the chamber.

In order to prevent any contamination of the various vessels or transfer chambers by air flowing into the system, the system is generously maintained at a pressure which is higher than the ambient pressure. In addition, the pressure is generally higher at an upstream part of the system, e.g. the pressure maintained in the dry hold chamber 22 will be higher than the pressure in the elevator space 30 which in turn will be higher than the pressure in the sealing space 31, which in turn is greater than the ambient pressure. In the event of a minor leak in the various vessels and chambers, the greater pressure within the vessels or chamber will prevent ambient and possibly contaminated air flowing into the system.

We claim:

1. A process for sterilizing a moisture sensitive product comprising; providing a closed sterilization system; maintaining said system in an aseptic condition by periodic decontamination with a disinfecting agent;

a) providing a sterilizable moisture sensitive product to be sterilized in an unsealed moisture impervious package, b) placing the product containing package in a first vessel, c) evacuating the first vessel, d) filling said first vessel with a gaseous sterilant, e) holding the product containing package in said first vessel until the product is sterilized, f) evacuating the gaseous sterilant from said first vessel, g) transferring the product containing package to a second vessel while maintaining said product containing package in a dry, pathogen free atmosphere and holding the product containing package in said second vessel until the product is substantially free of detectable moisture, h) transferring the product containing package to a third vessel while maintaining said product containing package in a dry pathogen free atmosphere, said third vessel having an atmosphere comprising a dry inert gas having a dew point of less than −30° C. and maintaining the package in a dry gas atmosphere until the package is sealed.

2. The process of claim 1 in which the dry inert gas in said third vessel is nitrogen having a dew point of −52° C.

3. A process for sterilizing a moisture sensitive medical product comprising; providing a closed sterilization system; maintaining said system in an aseptic condition by periodic decontamination with a disinfecting agent;

a) providing a sterilizable medical product in an unsealed moisture impervious package.

b) placing the medical product containing package in a first vessel, c) evacuating said first vessel, d) filling said first vessel with a gaseous sterilant, e) holding the medical product containing package in said first vessel until the medical product is sterilized, f) evacuating the gaseous sterilant from said first vessel, g) transferring the medical product containing package through a first transfer chamber to a second vessel while maintaining said medical product containing package in a dry pathogen free atmosphere, h) holding the medical product containing package in said second vessel at a temperature of from 48° to 52° C. cycling the atmosphere in said vessel by sequentially adding dry nitrogen to a pressure approximately 100 KPa followed by reducing the pressure to approximately 0.01 KPa until the medical product is substantially free of moisture, i) transferring the medical product containing package through a second transfer chamber to a third vessel while maintaining said medical product containing package in a dry pathogen free atmosphere, said third vessel having an atmosphere of a dry gas having a dew point of less than −30° C. and maintaining the package in a controlled air atmosphere having a dew point of not more than −30° C. until the package is sealed.

4. The process of claim 3 in which the first and second transfer chambers have an atmosphere of dry nitrogen having a dew point of −30° C. Immediately prior to the transfer of the medical product containing packages.

5. The process of claim 1 including the step of providing trays to retain packages of moisture sensitive products and providing a pallet to retain the trays and transferring the packages of moisture sensitive products through the vessels in said trays retained on said pallets.

6. The process of claim 1 in which the gaseous sterilant consists of ethylene oxide.

7. The process of claim 1 in which the gaseous sterilant comprises ethylene oxide.

* * * * *